(12) United States Patent
Thommen et al.

(10) Patent No.: US 8,764,790 B2
(45) Date of Patent: Jul. 1, 2014

(54) IMPLANT FOR OCCLUDING A BODY PASSAGE

(75) Inventors: Daniel Thommen, Zug (CH); Simon Furrer, Luzern (CH); Jérôme Bernhard, Zürich (CH); Lukas Christen, Luzern (CH); Silvia Egli, Schachen (CH); Franziska Gundi, Baar (CH); Marc Robert, Küssnacht (CH); Franz Suter, Baar (CH)

(73) Assignee: Carag AG (CH)

( * ) Notice: Subject to any disclaimer, the term of this patent is extended or adjusted under 35 U.S.C. 154(b) by 1289 days.

(21) Appl. No.: 10/588,325

(22) PCT Filed: Feb. 4, 2004

(86) PCT No.: PCT/CH2004/000059
§ 371 (c)(1),
(2), (4) Date: May 4, 2007

(87) PCT Pub. No.: WO2005/074813
PCT Pub. Date: Aug. 18, 2005

(65) Prior Publication Data
US 2007/0282430 A1      Dec. 6, 2007

(51) Int. Cl.
*A61B 17/08*      (2006.01)
(52) U.S. Cl.
USPC .................................................. 606/213
(58) Field of Classification Search
USPC ......... 606/213, 215–217, 151, 157, 158, 200; 623/23.72–23.76; 128/831, 843
See application file for complete search history.

(56) References Cited

U.S. PATENT DOCUMENTS

| | | | |
|---|---|---|---|
| 3,874,388 A | 4/1975 | King et al. | |
| 4,836,204 A | 6/1989 | Marble et al. | |
| 5,171,259 A | 12/1992 | Inoue | |
| 5,846,261 A * | 12/1998 | Kotula et al. | 606/213 |
| 5,976,174 A | 11/1999 | Ruiz et al. | |
| 6,117,159 A | 9/2000 | Buscemi et al. | |
| 6,355,052 B1 * | 3/2002 | Neuss et al. | 606/213 |
| 6,488,706 B1 | 12/2002 | Solymar et al. | |
| D493,223 S | 7/2004 | Solymar | |
| 6,949,116 B2 | 9/2005 | Solymar et al. | |
| 7,097,653 B2 * | 8/2006 | Freudenthal et al. | 606/213 |
| 2003/0149463 A1 * | 8/2003 | Solymar et al. | 623/1.1 |
| 2005/0043759 A1 * | 2/2005 | Chanduszko | 606/213 |

FOREIGN PATENT DOCUMENTS

| | | | | |
|---|---|---|---|---|
| EP | 0 474 887 A | | 3/1992 | |
| WO | WO 97/41779 A1 | | 11/1997 | |
| WO | WO 97/42878 | * | 11/1997 | A61B 17/00 |
| WO | WO 01/49185 A | | 7/2001 | |
| WO | WO 02/38051 A | | 5/2002 | |

OTHER PUBLICATIONS

European Search Report for EP 1994887 A1, Sep. 22, 2008.

* cited by examiner

*Primary Examiner* — Corrine M McDermott
*Assistant Examiner* — Christopher L Templeton
(74) *Attorney, Agent, or Firm* — McDonnell Boehnen Hulbert & Berghoff LLP

(57) ABSTRACT

An implant for occluding a passage in a circulatory system of a human body comprises elongate members (1) which can be twisted into fixation structures and at least two occluding bodies (2, 2') being attached to the elongate members (1) and being arranged at a distance to each other. This implant combines the advantages of a single occluding body implant with the advantages of a double occluding body implant.

13 Claims, 3 Drawing Sheets

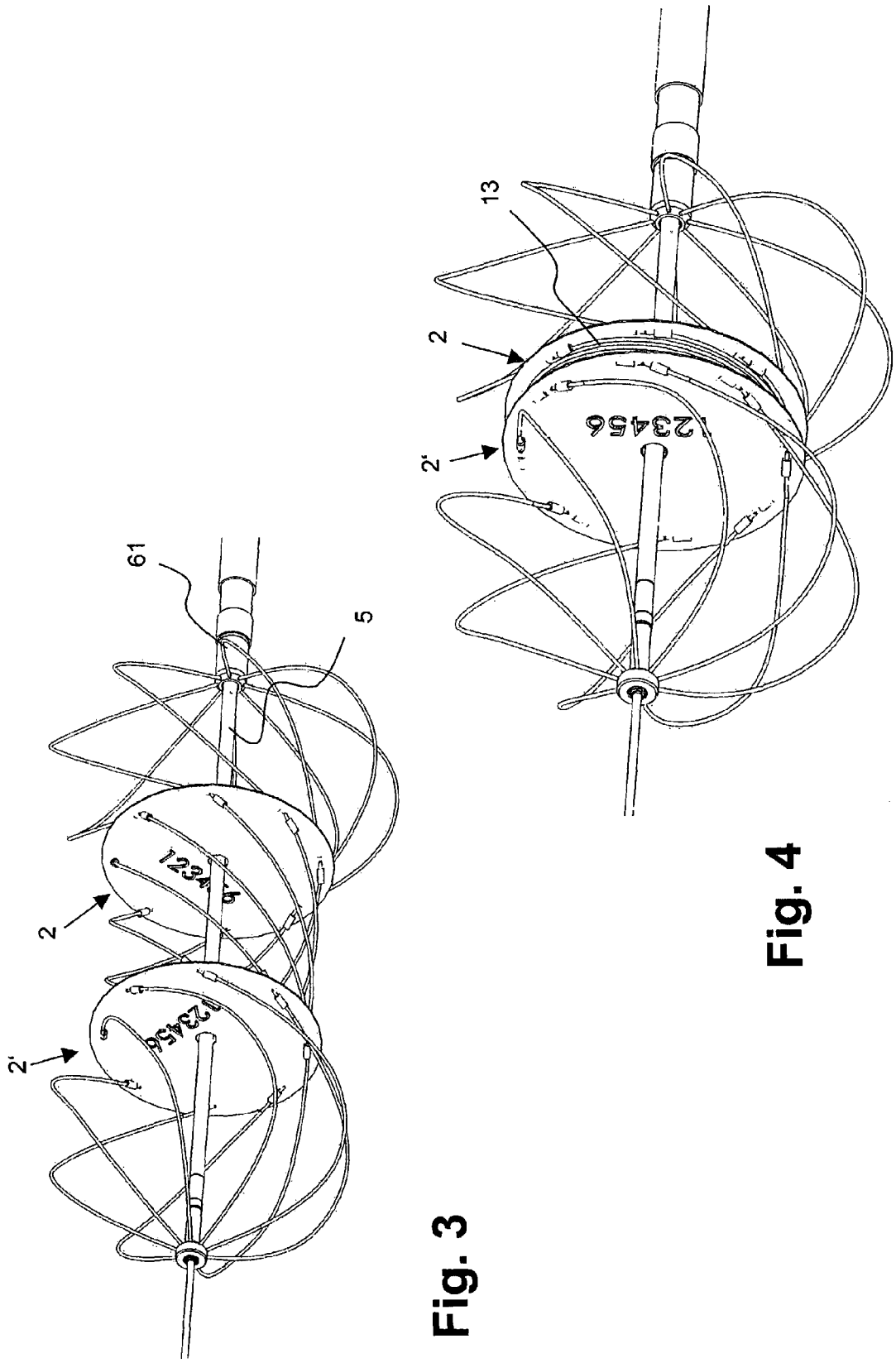

IMPLANT FOR OCCLUDING A BODY PASSAGE

FIELD OF THE INVENTION

The present invention generally relates to an implant for closing a passage in a circulatory system and more particular for closing a body passage of a human body, for example an aperture through the atrial septum or the ventricle septum of a heart or in a body channel.

BACKGROUND OF THE INVENTION

A well-working implant for occluding a passage in a circulatory system is disclosed in WO 02/38051. This implant has its particular application as a cardiological implant by means of which it is possible, for example, to close an aperture through the atrial septum or the ventricle septum of a heart. It is arranged to be deployed or built up (i.e., assembled) at a desired location in the body (e.g. the heart), in contrast to known other implants (e.g. so-called umbrellas and sails) that are instead extended as soon as the compressed umbrella leaves its insertion sheath.

This implant includes a plurality of thin wire-like elongate members each having a proximal and a distal end and being made of non-bendable material. The implant further comprises two holders to which the ends of the elongate members are attached. By reducing the distance between the two holders the elongate members are caused to execute a twisting motion yielding in a plurality of radially extending loops. When the two holders are interlocked with each other, the loops are fixed in a fixation structure which fixes the implant in the passage.

The implant further comprises an occluding body being fixed to the elongate members. This occluding body is deployed or expanded when the two holders are brought together and the passage is closed. In one embodiment, a balloon structure is expanded on both side of the passage, e.g. the atrial septum. In another preferred embodiment, a disk-shaped occluding body made of a flexible material is arranged in the middle between the two holders and hold in its expanded position by the twisted elongate members.

One of the advantages of using a single occluding body implant is that only one occluding body has to be opened and placed in the passage. However, sometimes, the opening in the passage is such, that the occluding body is not big enough to securely close the passage. It is then preferred to locate an occluding body on both sides of the septum each.

Such an implant is shown in U.S. Pat. No. 5,171,259. It comprises a pair of patches each consisting of a resilient, foldable annular frame and a piece of cloth stretched over and fixed to the frame. The patches are so arranged as to face each other across a gap and sewed together concentrically with a thread slightly inwardly of the outer circumferential edge thereof in such a manner that as the thread is pulled the two patches are moved so as to approach each other. This implant is introduced into the passage using a catheter. First the first patch is released from the catheter and opened, then the catheter is retrieved a bit before the second patch is released and opened. U.S. Pat. No. 4,836,204 discloses an implant comprising two balloons, wherein they are also opened one after the other. These implants have the disadvantages, that two occluding bodies must be placed and opened in the passage at two different times during surgery.

U.S. Pat. No. 6,117,159 shows a catheter delivered device to close a septal defect, the implant comprising a shaft with concentric parallel cuts through the wall of the device which create flattened support struts. The centre of the support struts move radially away from the axis in a hinge like fashion in response to the movement of the device's proximal and distal ends toward the centre of the device. This device does not comprise an occluding body but it is coated with determinants which can improve tissue growth.

SUMMARY OF THE INVENTION

It is an object of the present invention to provide an improved implant for occluding a passage in a circulatory system, especially of a human body.

The foregoing object is achieved by means of an implant according to the features of claim 1.

The inventive implant comprises
a plurality of thin elongate members each having a first end and a second end;
a first holder to which the first ends of the elongate members are attached;
a second holder to which the second ends of the elongate members are attached, the elongate members being attached to the first and second holders;
a first occluding body being attached to the elongate members;
the implant forming in a first state an elongated article extending along a longitudinal axis, the implant being adapted in the first state for insertion into the circulatory system and the implant being adapted to be brought into a second state in the circulatory system, wherein the distance between the holders being reduceable in a manner to cause the elongate members to execute a twisting motion relative to the axis to yield a plurality of generally radially extending loops forming at least one fixation structure, thereby increasing a cross-section of the occluding body and the at least one fixation structure being fixable in the second state,
wherein
the implant comprises at least one second occluding body being attached to the elongate members at a distance to the first occluding body and wherein the distance between the first and the second occluding body is reduceable by reducing the distance between the two holders, wherein at least one of the group of the following fixation structures is formed: a first of said fixation structure between the first occluding body and the first holder and a second of said fixation structure between the second occluding body and the second holder.

Preferably, both fixations structures are built up when the holders are brought together.

It was found, that this occluder comprising at least two occluding bodies can be opened in a better guided way into its second state. The elongate member are bended more willingly into their looped twisted fixation structure. The inventive occluder therefore demands less skill and experience to be introduced and located at the right place in the passage. Even when the lengths of the elongate members are chosen such that the first and the second occluding body do not open at the same time and/or the first and second fixation structure are not formed at the same time, they still are opened or formed respectively in the same movement, i.e. by bringing the two holders together.

Since this implant comprises at least two occluding bodies, which can be built up on both sides of passage at the same time or with the same movement respectively, the advantages of the known double bodies occluder and the advantages of the single body occluder can be combined, without having the disadvantages thereof.

These and other advantages and objects achieved by the present invention will be further appreciated and understood upon consideration of the following detailed description of preferred embodiments taken in conjunction with the drawings in which:

BRIEF DESCRIPTION OF THE DRAWINGS

FIG. 3 the implant according to FIG. 1 in a first in-between state;

FIG. 4 the implant according to FIG. 1 in a second in-between state;

PREFERRED EMBODIMENTS

The device according to the invention is based on the implants disclosed in WO 02/38051, the disclosure thereof is incorporated in this description by reference.

The inventive device is employed as an implant for closing an internal passage, for example, an aperture in the atrial septum or the ventricle septum of a heart, or in another human or animal body channel which one wishes to close. The implant is compressible for insertion through a delivery mechanism, such as a body vein, and is deployable or expansible for occluding the passage in the circulatory system when arrived at the position of the intended closing spot.

Figure 1:
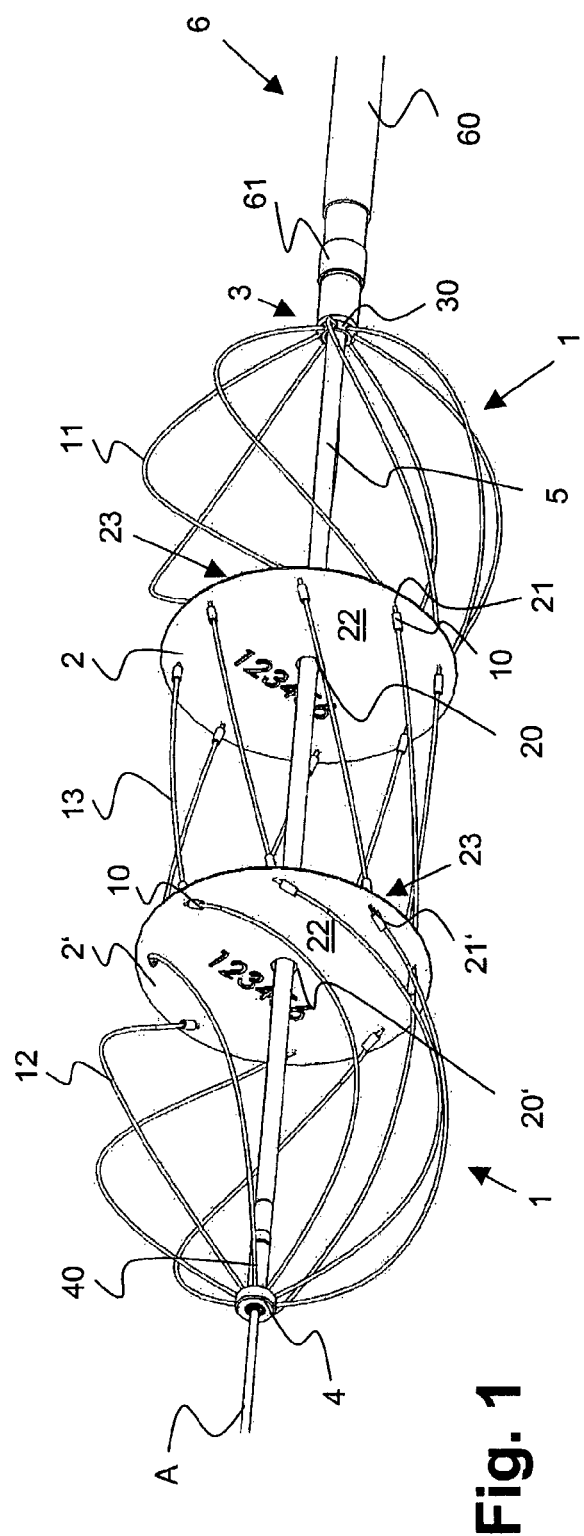
FIG. 1 shows a perspective view of an implant according a first embodiment of the invention in an initial state.

FIG. 1 shows the implant of the present invention in an initial state, i.e., before the device is applied to the passage in a circulatory system, compressed during its insertion and deployed after it has arrived at the intended closing spot.

The implant comprises a plurality of thin elongate members 1, such as wires or threads, a first occluding body 2, at least one second occluding body 2', a first holder 3 and a second holder 4. The implant extends along a virtual longitudinal axis A.

The elongate members 1 are attached with their first, proximal ends to the first holder 3 and with their second distal ends to the second holder 4. Proximal means near to the surgeon, and distal near to the patient. The members 1 can be attached in a pre-twisted or un-twisted manner. The elongate members 1 are usually made of a thin stiff generally inextensible, but somewhat flexible material. For example, they can be made of nitinol or another non-bendable material. Preferably they are made of Phynox, i.e. a cobalt-chromium-nickel alloy, or of a plastic. The figure shows eight elongate members 1. This is the preferred number, but it should be understood that the number of members can be varied.

The first and second occluding bodies 2, 2' are located between the two holders 3, 4 and extend in a generally radial manner from the longitudinal axis A. They comprise a central hole 20, 20' each. In their circumferential region, the occluding bodies 2, 2' are attached to the elongate members 1. The bodies 2, 2' comprise outer holes 21, 21' through which the elongate members 1 extend. The elongate members 1 comprise thickened portions 10 arranged on both sides of the outer holes 21, 21' of the occluding bodies 2, 2' which serve to capture and mount the occluding bodies 2, 2', so that the position of the occluding bodies 2, 2' between pairs of two respective thickened portions 10 is fixed within spaces defined by pairs of said thickened portions 10.

The occluding bodies 2, 2' divide each of the elongate members 1 in three portions. A first portion 11 lays between the first holder 3 and the first occluding body 2, a second portion 12 between the second occluding body 2' and the second, distal holder 4 and the third portion 13 between the first and the second occluding body 2, 2'.

Preferably, at least the first and second portions 11, 12 of each elongate member 1 have approximately the same length. Preferably, also the third portions 13 have the same length. However, all of them can also have different lengths.

The occluding bodies 2, 2' are made of a flexible, for example fabric-like, material consistent with surgical use. A preferred material is Polyester. They can also be made of a biodegradable or bioabsorbable material. Preferably, both occluding bodies 2, 2' are made of the same material and have the same sizes. However, it is also possible to use different kinds of first and second occluding bodies.

The occluding bodies 2, 2' however should have a distal face 22 oriented toward the second holder 4 and a proximal face 23 oriented toward the first holder 3. They have at least in their deployed condition, preferably also in their initial position an at least approximately disk-shaped form, preferably a circular shape. Since they are made of flexible material, they can be compressed into a compressed form, for example being similar to an umbrella.

Figure 2:
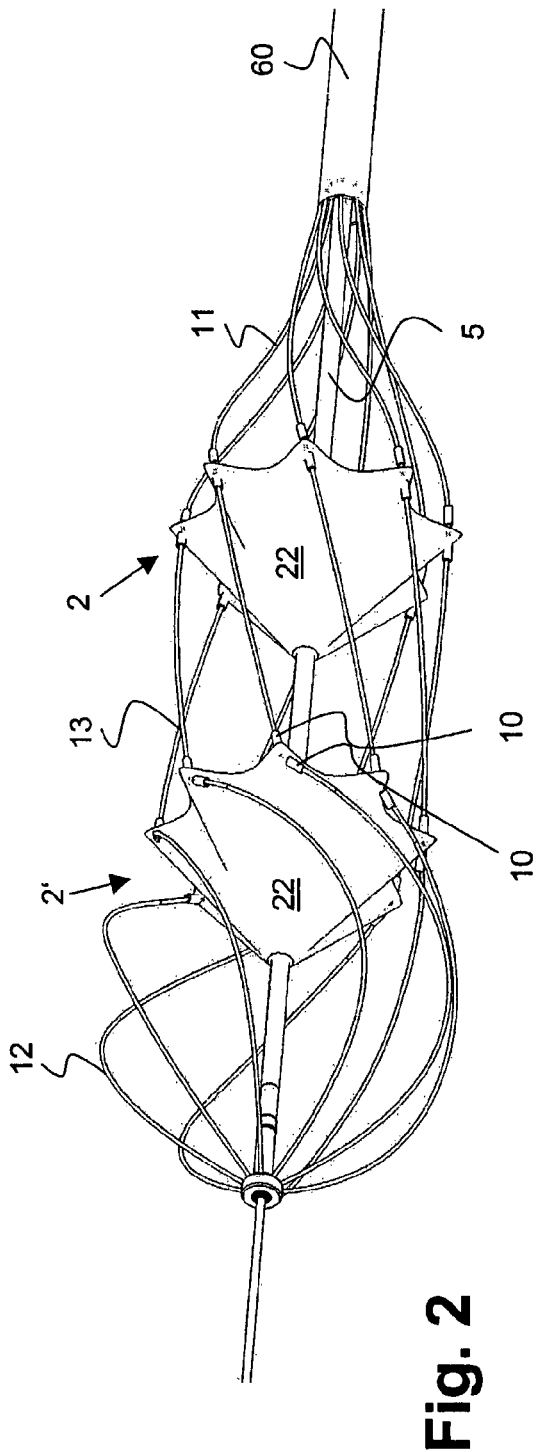
FIG. 2 the implant according to FIG. 1 in a partly compressed state.

In order to introduce the implant into the passage, a carrier rod 5 and a driving implement 6, such as a catheter or another suitable sleeve, can be used. The implant can be inserted intravenous. However, it can also be introduced through the esophagus or other appropriate living body channels. The carrier rod 5 extends slidably moveable through the first holder 1 and the central holes 20, 20' in the first and second occluding body 2, 2' and is fixedly but removably held in the second holder 4. FIG. 2 shows the implant mounted on the rod 5 and being partly compressed by the sleeve 60 of the driving implement 6. Compressing the implant causes the occluding bodies 2, 2' to reduce their outer cross-section or diameter.

In a first totally compressed state the implant is introduced into the passage. When it is placed at the requested location, the sleeve 60 is pulled back. Second, a pushing rod 61 is used to push the first holder 3 towards the second holder 4, and/or the carrier rod 5 is pulled back thereby moving the second holder 4 closer to the first holder 3 which is in this case held in place. Because of the two holders 3, 4 approaching each other, the elongate members 1 are bended and finally twisted into fixation structures. The occluding bodies 2, 2' are at the same time deployed and regain their disk-shaped form.

Figure 5:
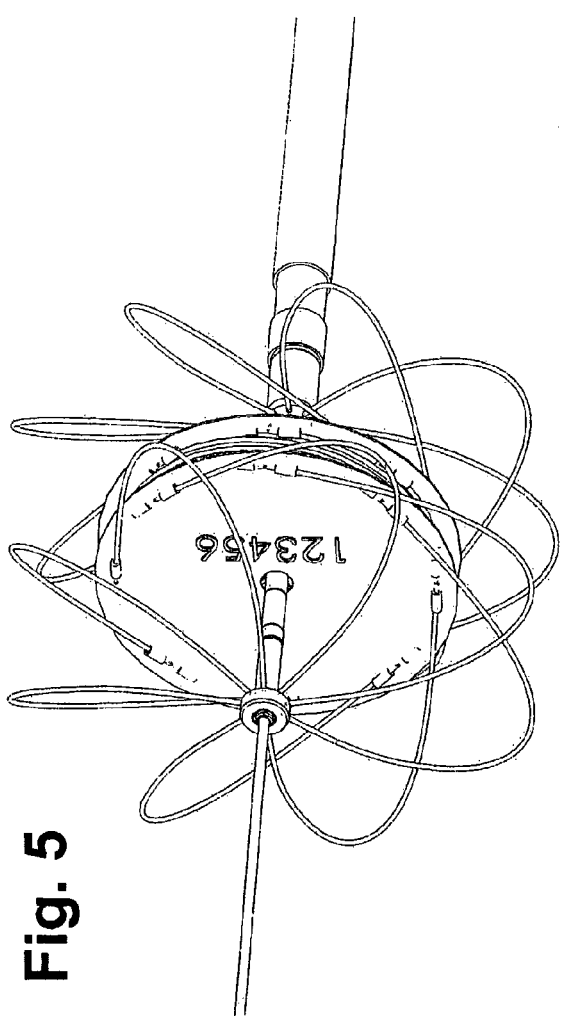
FIG. 5 the implant according to FIG. 1 in a third in-between state.

FIGS. 3 to 5 show different in-between states of the implant during this movement. Moving the two holders 3, 4 together at first causes the first and second portions 11, 12 of the inextensible elongate members 1 to assume a gently outwardly bowed configuration each with respect to the longitudinal axis A. The third portions 13 are bend as well. Further moving the first holder 3 towards the second holder 4 causes the first and second portions 11, 12 of the elongate members 1 to assume a more bowed, almost semi-circular shape. At some stage, the non-bendable elongate members 1 pass through a critical point, whereupon the first and second portions 11, 12 snap into a generally radially-extending loops, yielding a somewhat concave petalshaped structure each. This means that the first and second portions 11, 12 finally twist and each portion 11, 12 form together with same portion of the other elongate members 1 a first and second fixation structure respectively. These fixations structures have a shape similar to a flower or a windwheel. The third portions 13 are bended less than the first and second portions 11, 12.

Preferably, the first and second portions 11, 12 are twisted in the same way and the first and second fixation structures obtained thereof have the same outer diameter. The third portion 13 is normally only bended like a spring, but not twisted like the first and second portions 11, 12. The third portion forms in this second state a bended structure which has preferably an outer diameter having approximately the same size than the diameter of the cross-section of the two occluding bodies 2, 2'. If the two occluding bodies 2, 2' have different sizes, the bended structure can have the same size as one of the occluding bodies 2, 2', wherein it can have the size of the smaller or the bigger one or a size in-between.

Figure 6:
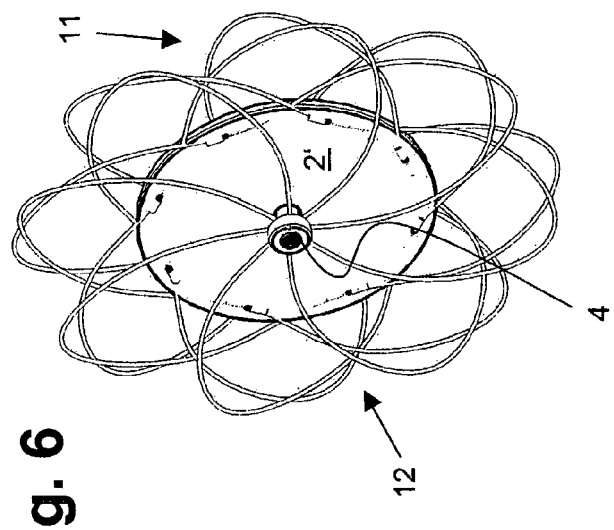
FIG. 6 the implant according to FIG. 1 in a second deployed state.

FIG. 6 shows the implant in its final and second state. In this state, the implant is placed at the passage, the fixations structures are formed and the occluding bodies 2, 2' are deployed. The occluding bodies 2, 2' are stiffened and form a fluid tight closing body on both sides of the septum. The form of the occluding bodies 2, 2' can be the same as in the initial position or it can be expanded. Their location in the passage is fixed by the fixation structures formed by the twisted and fixed elongated members 1.

One way to keep the implant in this second state, i.e. to fix the elongate members 1 in their twisted position, is to attach the two holders 3, 4 to each other. In this embodiment, the two holders 3, 4 therefore comprise a locking mechanism, preferably consisting of snap together members 30, 40, lock the elongate members 1 in their twisted position. These locking means are already described in WO 02/38051 and its disclosure will therefore not be repeated here.

Figure 7:
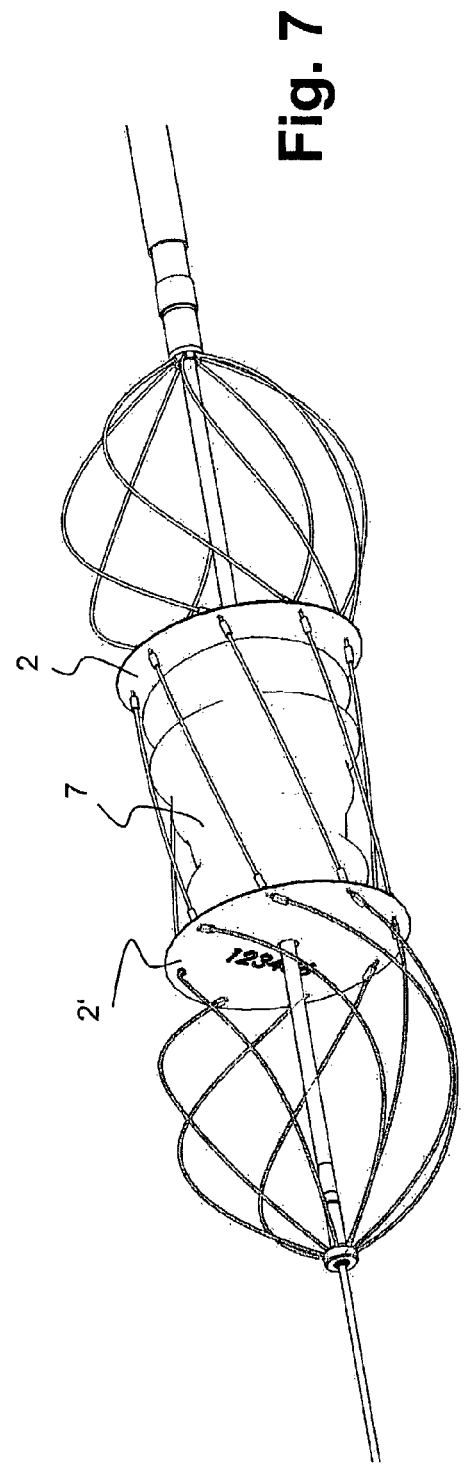
FIG. 7 a perspective view of an implant according to the invention according to a second embodiment.

FIG. 7 shows another preferred embodiment. This embodiment comprises a compressible body 7 made of a compressible material, such as a cotton swab. This body 7 is located between the two occluding bodies 2, 2' and hold between the third portions 13 of the elongate members 1. This compressible material helps to occlude the passage.

The inventive implant combines the advantages of a single occluding body implant with the advantages of a double occluding body implant.

LIST OF REFERENCE NUMBERS 1 elongate members
10 thickened portion
11 first portion
12 second portion
13 third portion
2 first occluding body
2' second occluding body
20 central holes
20' central holes
21 outer holes
21' outer holes
22 distal face
23 proximal face
3 first holder
30 first locking means
4 second holder
40 second locking means
5 carrier rod
6 driving implement
60 sleeve
61 pushing rod
7 compressible body
A longitudinal axis

The invention claimed is:

1. An implant for occluding a passage in a circulatory system, the implant comprising:
    a plurality of elongate members each having a first end and a second end, wherein the plurality of elongate members are stiff and thin;
    a first holder to which the first ends of the plurality of elongate members are attached;
    a second holder to which the second ends of the plurality of elongate members are attached, and the first and second holders comprising a locking mechanism;
    a first occluding body being attached to the plurality of elongate members;
    a second occluding body being attached to the plurality of elongate members at a distance to the first occluding body and wherein the distance between the first occluding body and the second occluding body is reducible by reducing a distance between the first and the second holders;
    the first and second occluding bodies being formed as thin disk-shaped elements separate from the plurality of elongate members and made of a flexible material, wherein the plurality of elongate members have first portions being arranged between the first holder and the first occluding body, second portions being arranged between the second holder and the second occluding body and third portions being arranged between the first and the second occluding bodies, wherein the first and the second occluding bodies divide the plurality of elongate members into the first, the second and the third portions; and
    wherein the implant forms in a first state an elongated article extending along a longitudinal axis, wherein the first and the second occluding bodies have in this first state a compressed form, the implant being adapted in the first state for insertion into the circulatory system and the implant being adapted to be brought into a second state in the circulatory system, wherein the distance between the first and the second holders is reducible in a manner that causes the first portions and the second portions of the plurality of stiff and thin elongate members, when passing a critical point, to execute a twisting motion relative to the longitudinal axis thereby snapping into a plurality of generally radially extending loops, the first portions thereby forming a first fixation structure and the second portions thereby forming a second fixation structure, and the first and the second occluding bodies thereby being deployed and forming closing bodies in the second state, wherein a cross-section of the first and the second occluding bodies having in this second state a disk-shaped form, with the third portions of each of the plurality of elongate members collapsing upon themselves upon formation of the first and the second fixation structures to bring the first and the second occluding bodies into adjacent facial proximity, wherein at least one of the first and second fixation structures is fixable in the second state, wherein the first and the second holders are interlocked with each other via the locking mechanism to keep the implant in the second state, and wherein the plurality of elongate members penetrate through the first and the second occluding bodies.

2. The implant according to claim 1, wherein the first and the second portions of each of the plurality of elongate members have approximately the same length.

3. The implant according to claim 1, wherein the first, the second and the third portions of each of the plurality of elongate members have approximately the same length.

4. The implant according to claim 1, wherein the third portions of each of the plurality of elongate members are not twisted like the first and the second portions of each of the plurality of elongate members.

5. The implant according to claim 1, wherein in the second state the third portions of each of the plurality of elongate members form a bended structure with an outer diameter having approximately the same size as a diameter of the cross-section of at least one of the first or the second occluding bodies.

6. The implant according to claim 1, wherein in the second state the cross-sections of the first and the second occluding bodies have the same size.

7. The implant of claim 1, wherein the first and the second occluding bodies have an at least approximately circular shape.

8. The implant according to claim 1, wherein the plurality of elongate members have the same length.

9. The implant according to claim 1, wherein a compressible body is arranged between the first and the second occluding body.

10. The implant according to claim 1, wherein the plurality of elongate members are wires or threads.

11. The implant of claim 1, wherein the first and the second fixation structures each extend radially beyond a perimeter of the adjacent occluding body.

12. An implant for occluding a passage in a circulatory system, the implant comprising:
a plurality of elongate members each having a first end and a second end, wherein the plurality of elongate members are stiff and thin;
a first holder to which the first ends of the plurality of elongate members are attached;
a second holder to which the second ends of the plurality of elongate members are attached, and the first and second holders comprising a locking mechanism;
a first occluding body being attached to the plurality of elongate members;
a second occluding body being attached to the plurality of elongate members at a distance to the first occluding body and wherein the distance between the first occluding body and the second occluding body is reducible by reducing a distance between the first and the second holders;
the first and second occluding bodies being formed as thin disk-shaped elements separate from the plurality of elongate members and made of a flexible material, wherein the plurality of elongate members have first portions being arranged between the first holder and the first occluding body, second portions being arranged between the second holder and the second occluding body and third portions being arranged between the first and the second occluding bodies, wherein the first and the second occluding bodies divide the plurality of elongate members into the first, the second and the third portions; and
wherein the implant forms in a first state an elongated article extending along a longitudinal axis, wherein the first and the second occluding bodies have in this first state a compressed form, the implant being adapted in the first state for insertion into the circulatory system and the implant being adapted to be brought into a second state in the circulatory system, wherein the distance between the first and the second holders is reducible in a manner that causes the first portions and the second portions of the plurality of stiff and thin elongate members, when passing a critical point, to execute a twisting motion relative to the longitudinal axis thereby snapping into a plurality of generally radially extending loops, the first portions thereby forming a first fixation structure and the second portions thereby forming a second fixation structure, and the first and the second occluding bodies thereby being deployed and forming closing bodies in the second state, wherein a cross-section of the first and the second occluding bodies having in this second state a disk-shaped form, with the third portions of each of the plurality of elongate members collapsing upon themselves upon formation of the first and the second fixation structures to bring the first and the second occluding bodies into adjacent facial proximity, wherein at least one of the first and second fixation structures is fixable in the second state, wherein the first and the second holders are interlocked with each other via the locking mechanism to keep the implant in the second state, and wherein the first and the second occluding bodies comprise holes and wherein the plurality of elongate members are extending through the holes.

13. The implant according to claim 12, wherein the plurality of elongate members comprise thickened portions arranged on both sides of the first occluding body and the second occluding body.

* * * * *